United States Patent [19]

Johnson, Jr.

[11] 4,280,489
[45] Jul. 28, 1981

[54] ANKLE BRACE

[76] Inventor: Glenn W. Johnson, Jr., 10 Friar Tuck Cir., Summit, N.J. 07901

[21] Appl. No.: 141,925

[22] Filed: Apr. 21, 1980

Related U.S. Application Data

[63] Continuation of Ser. No. 894,087, Apr. 6, 1978, abandoned.

[51] Int. Cl.³ .............................................. A61F 3/00
[52] U.S. Cl. ................... 128/80 H; 128/166
[58] Field of Search ............... 128/80 H, 165, 166, 128/DIG. 20

[56] References Cited

U.S. PATENT DOCUMENTS

| 487,492 | 12/1892 | Pugsley | 128/166 |
|---|---|---|---|
| 1,465,233 | 8/1923 | Posner | 128/166 |
| 2,694,395 | 11/1954 | Brown | 128/DIG. 20 |
| 2,774,152 | 12/1956 | Alber | 128/DIG. 20 |
| 2,830,585 | 4/1958 | Weiss | 128/166 |

Primary Examiner—John D. Yasko

[57] ABSTRACT

There is provided a generally U-shaped stirrup member having a base portion and a pair of opposed sidewall portions attached to the base portion. A pair of air-inflatable liners or airbags are disposed interiorly of the stirrup member in juxtaposed relation to the sidewall portions, respectively, and extend in a substantially coextensive manner therewith. By this arrangement, when the stirrup member is fitted about the lower extremity, the sidewall portions engage the lateral and medial portions of the lower extremity. A plurality of fastener straps are provided to maintain the sidewall portions of the stirrup member snuggly fitted about the lower leg above the ankle. Means are provided for facilitating inflation of each airbag after the stirrup member has been fitted about the lower extremity and the fastener straps have been engaged.

8 Claims, 3 Drawing Figures

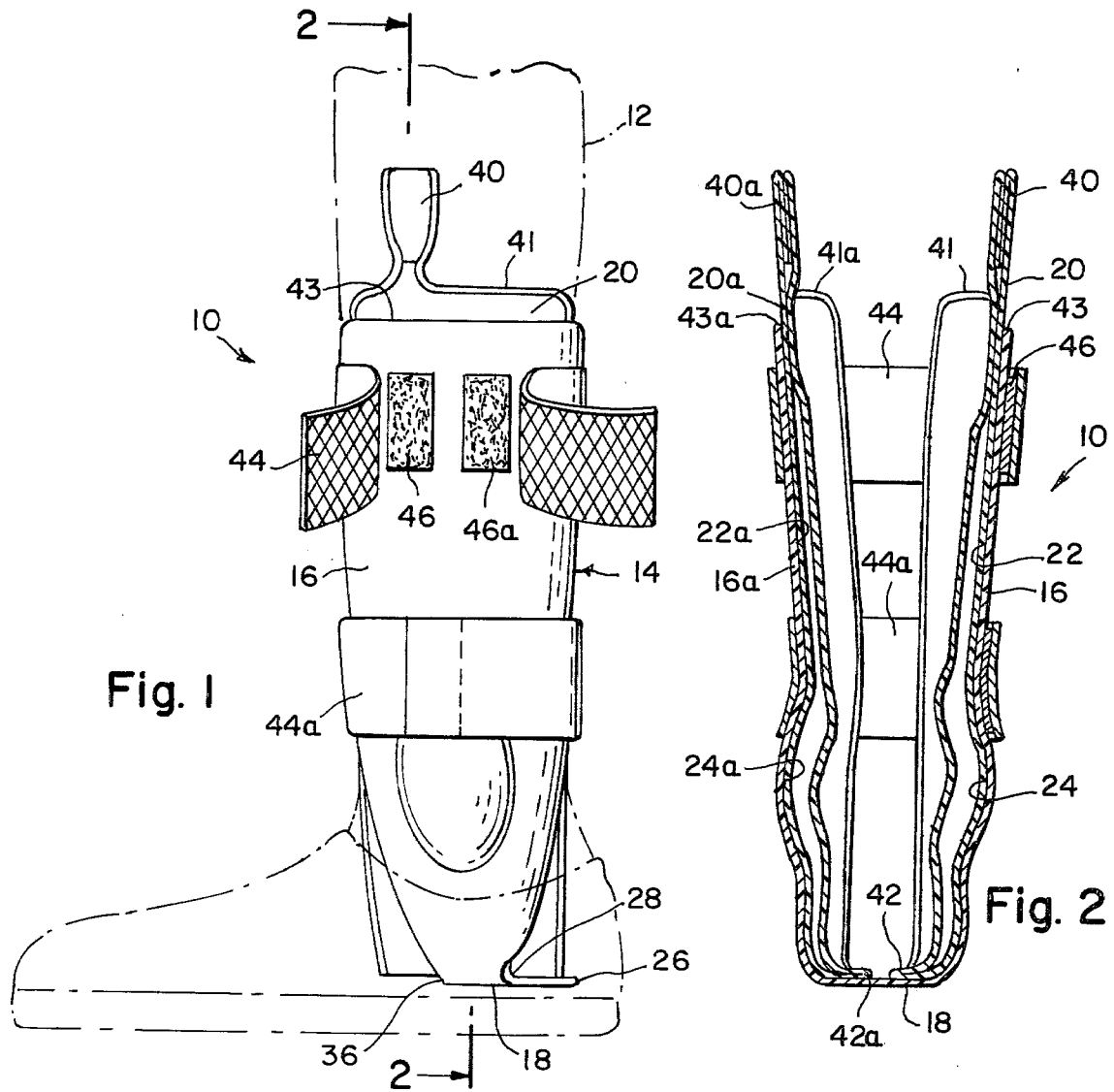
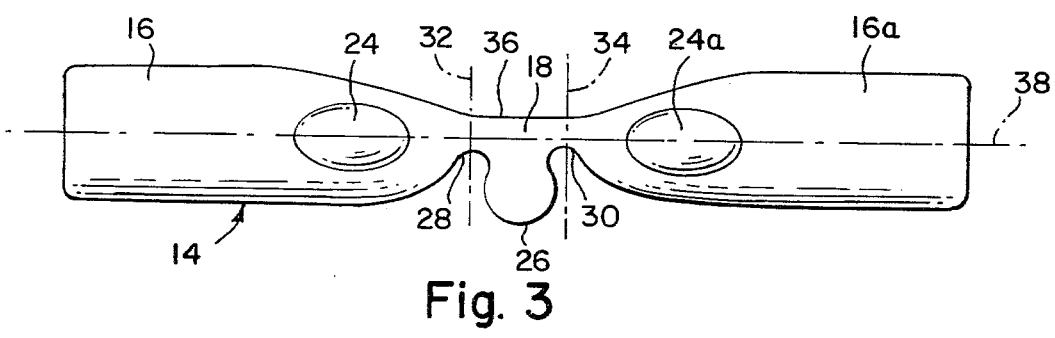

ANKLE BRACE

This is a continuation of application Ser. No. 894,087, filed Apr. 6, 1978, now abandoned.

The present invention relates generally to orthopedic devices and more particularly, to ankle braces for stabilizing the ankle against inversion and eversion without limiting normal planto flexion and dorsiflexion of the ankle.

In the management of certain injuries to the lower extremities such as fractures of the tibia and fibula, malleolar fractures, or severe ankle sprains it is common to completely immobilize the lower extremity (following open or closed reduction in the case of fractures) by use of the well known molded plaster or resin cast.

Once the injured extremity has become stable however, it has been found that recovery may be effected more rapidly by gradually and progressively permitting the extremity to bear weight and undergo other permitted exercises. Thus, for example, during a second stage of management, a walking heel may be attached to a long plaster cast or the latter replaced by a shorter unit or by a walking cast specifically adapted to facilitate such maneuvers. One form of walking cast commercially available under the trademark AIRCAST and described in my prior U.S. Pat. No. 3,955,565, consists of a pair of radially telescoping plastic shell members fitted snuggly about the lower extremity and having disposed interiorly thereof a plurality of inflated airbags which fill the voids between the outer shell members and the lower extremity. While the latter form of walking cast has the advantage of being removable and of being readjustably conformable to the lower extremity thereby promoting comfort, it still substantially immobilizes the lower extremity when being worn.

A need exists therefore, for an orthopedic device which permits substantially normal planto flexion and dorsiflexion movements of the ankle, but limits inversion and eversion thus stabilizing the ankle, and which incorporates the advantages of being removable and easily reapplied, and further, of being readjustable to conform to the lower extremity thus promoting comfort.

It is the principle object of the present invention to meet the foregoing need by providing such an orthopedic device.

It is yet another object of the present invention to provide a removable brace for the lower extremity which facilitates planto flexion and dorsiflexion of the ankle while stabilizing the latter against inversion and eversion and which may be worn inside a conventional shoe to facilitate normal walking or running movements of the lower extremity.

It is still yet another object of the present invention to provide a removable ankle brace having air-inflated flexible liner means and which upon normal walking movement and dorsiflexion of the ankle causes a momentary increase in the internal pressure of a portion of the liner which latter encourages blood circulation and expedites healing of the lower extremity.

It is yet still another object of the present invention to provide an ankle brace which facilitates the progressive management method of treating injuries to the lower extremity.

Toward the accomplishment of these and additional objects and advantages the present invention, briefly described, comprises a generally U-shaped stirrup member having a base portion and a pair of opposed sidewall portions attached to the base portion. A pair of air-inflatable liners or airbags are disposed interiorly of the stirrup member in juxtaposed relation to the sidewall portions, respectively, and extend in a substantially coextensive manner therewith. The bottom portion of each airbag may be folded inwardly to at least partially overlie a portion of the upper surface of the stirrup member base portion. By this arrangement, when the stirrup member is fitted about the lower extremity or foot, the heel of the latter rests on the bottom, inwardly folded portions of the airbags. A plurality of fastener straps are provided to maintain the sidewall portions of the stirrup snuggly fitted about the lower leg above the ankle. Finally, means are provided for facilitating inflation of each airbag after the stirrup has been fitted about the lower extremity as hereinaforesaid.

The foregoing and still other features and advantages of the present invention as well as a more complete understanding thereof will be made apparent from a study of the following detailed description of the invention in connection with the accompanying drawing wherein:

FIG. 1 is a side view in elevation of the orthopedic device according to the present invention depicted in fitted engagement about the lower extremity of a human;

FIG. 2 is a sectional view of the orthopedic device according to the present invention taken along line 2—2 of FIG. 1; and FIG. 3 is an unfolded plan view in reduced scale of the stirrup member of the orthopedic device of FIGS. 1 and 2.

Turning now to FIGS. 1 and 2, there is schematically shown the orthopedic device of the present invention which in its preferred form comprises an ankle brace generally represented by reference numeral 10. For purposes of illustrating the present invention, the ankle brace 10 is shown in FIG. 1 fitted about the right lower extremity of a human with the lower extremity being indicated diagramatically in outline form by broken lines. The term "lower extremity" as used herein should be interpreted broadly to include the foot, the ankle, and the lower leg.

Ankle brace 10 comprises a generally U-shaped stirrup member 14 which in the embodiment shown is of one-piece construction having a pair of opposed sidewall portions 16, 16a integrally joined to a base portion 18, and a pair of air-inflatable, flexible liners or airbags 20, 20a disposed respectively on the inwardly facing surfaces 22, 22a of opposed sidewall portions 16, 16a in a generally juxtaposed manner coextensive therewith. Each sidewall portion 16, 16a extends longitudinally from base portion 18 and has an arcuate transverse cross-sectional shape sufficient to conform generally to the circumferential contour of the lower leg and ankle. In addition, the width of each sidewall portion gradually tapers from a minimum where it joins base portion 18 to a maximum at approximately the half-way point of its longitudinal extent, and then extends at substantially constant width to the remotely extending upper edge thereof substantially as shown in FIGS. 1 and 3. In order to accomodate the protruding lateral and medial malleolus on either side of the ankle, respectively, each sidewall portion 16, 16a includes therein respectively, a corresponding recess or dished portion 24, 24a defining a generally oblong shaped cavity disposed in each inner surface 22, 22a with each oblong-shaped recess or cavity having its major axis extending generally parallel to the longitudinal axis of each corresponding side portion. Each recess is purposely made large enough so that a stirrup member of one standard size will fit the lower extremities of many different subjects notwithstanding significant differences in age or physical size.

Further, since the medial malleolus typically has greater elevation than the lateral malleolus, it will be observed that recess 24 corresponding to the side portion of medial (tibial) aspect is located or spaced a slightly greater distance above base portion 18 than is recess 24a corresponding to the side portion of lateral (fibular) aspect. Accordingly, on an ankle brace adapted for use on a left lower extremity, a mirrored-image configuration would be required.

The upwardly facing surface of base portion 18 serves as a support for the heel and to this end its rearwardly facing boundary has a rounded contour 26 to conform generally to that of the heel substantially as shown in FIG. 3. Rounded contour 26 smoothly joins a pair of smaller radiused curved sections 28, 30 which latter define a pair of necked-down portions between the sidewall portions 16, 16a and the base portion 18. The necked-down portions in turn, define a pair of flexural axes 32, 34 about which each sidewall portion 16, 16a may be flexurally displaced relative to base portion 18. In addition, curved sections 28, 30 relieve stresses sufficiently to permit slight flexural displacement of sidewall portions 16, 16a relative to base portion 18 about an axis (not shown) perpendicular to axes 32, 34 and normal to the plane of the paper as viewed in FIG. 1. The forwardly facing edge 36 of base portion 18 has a relatively straight contour generally parallel to the central longitudinal axis 38 of each side portion 16, 16a as viewed in FIG. 3 and terminates at a point slightly beyond this central axis so that base portion 18 has a longitudinal extent sufficient to firmly support the heel bone (calcaneous), but is not long enough to limit planto flexion or dorsiflexion of the ankle.

Stirrup member 14 may advantageously be fabricated from a relatively thin sheet of synthetic thermoplastic polymeric resinous material with the sheet preferably having a thickness in the range of about 30 mils to 100 mils. A flat stirrup member blank is cut to shape following the contour outline substantially as shown in FIG. 3 and then placed in a conventional press or other forming device where under heat and pressure the sidewall portions 16, 16a are formed into an upright position normal to base portion 18, the transverse arcuate curvature is imparted to each sidewall portion, and the recesses 24, 24a are formed in each sidewall portion to achieve the resulting shape substantially as shown in FIGS. 1 and 2. Alternatively, the stirrup member 14 may be formed by injection molding in a well known manner. Exemplary thermoplastic materials suitable for use in fabricating stirrup member 14 in either foregoing manner may be obtained commercially from Rhom and Haas Co. under the trademark KYDEX; General Electric Co. under the trademark LEXAN; and Borg-Warner Corporation under the trademark CYCOLAC. Polypropylene which is also widely available commerically may also be employed as a suitable starting material.

Airbags 20, 20a are preferably similar to those fully disclosed in my copending application Ser. No. 842,961, filed Oct. 17, 1977, entitled "SELF-SEALING VALVE", which copending application is hereby incorporated herein and made part hereof by this reference. As disclosed in my copending application, Ser. No. 842,961, each airbag comprises a generally elongated, flattened inflatable bladder fabricated as by superimposing two sheets of a relatively thin, flexible material such as vinyl plastic with each sheet having a thickness of about 12 mils, and then heat sealing the sheets together along their common peripheral edges. In addition, each airbag 20, 20a includes a self sealing valve 40, 40a to facilitate inflation thereof with pressurized air and to automatically seal each airbag after it has been internally pressurized. Since the details of self sealing valves 40, 40a form no part of the present invention, they will not be further described herein, interested readers being directed instead to my copending application for a fuller description thereof. Of course, it will be appreciated that the present invention may be practiced by employing known inflatable bladders having suitable valves other than described in my copending application, Ser. No. 842,961.

Generally speaking, each airbag 20, 20a is sized and shaped so that when they are positioned in a juxtaposed coextensive manner relative to a corresponding confronting inside surface 22, 22a of each sidewall portion 16, 16a, the upper edge 41, 41a of each airbag extends slightly above the upper edge 43, 43a of each sidewall portion 16, 16a and the bottommost portions 42, 42a of each airbag are bent inwardly toward each other so as to overlie in a coextensive manner corresponding portions of the upwardly facing surface of base portion 18. By this arrangement, the heel of the lower extremity will rest on and engage the bottommost, inwardly bent portions 42, 42a of each airbag 20, 20a as will be explained in more detail below.

Preferably, each airbag is maintained in position relative to the inside surface 22, 22a of each sidewall portion and relative to the upwardly facing surface of base portion 18 substantially as shown in FIGS. 1 and 2 by means of a double faced adhesive patch or plurality of such patches, or other suitable fastening means disposed between each airbag and its corresponding confronting surface 22, 22a of sidewall portions 16, 16a.

Also, if desired a sponge rubber heel pad (not shown) such as is available commercially under the trademark DR. SCHOLL may be secured by an adhesive to the upper surface of the base portion 18 in an overlying position relative to the two inwardly bent portions 42, 42a of each airbag.

In order to maintain the ankle brace 10 in proper fitting engagement about the lower extremity, a pair of longitudinally spaced, circumferentially extending fastener strap members 44, 44a are provided. Preferably, each fastener strap member is of the well known woven fabric construction sold under the trademark VELCRO and is adapted to cooperate with a pair of circumferentially spaced fastener patch elements 46, 46a having the known VELCRO type hook-like extensions thereon with the patch elements being adhesively secured in a conventional manner to the exterior surface of side portion 16 in the position generally shown in FIG. 1 with respect to upper strap 44. As is also shown in FIG. 1 with respect to fastener strap 44, one end of each fastener strap is adapted to matingly engage a corresponding patch element so that the strap may then be drawn and tensioned snuggly around the exterior of both sidewall portions 16, 16a in a circumferential manner and the other end of the fastener strap attached to engage the other patch element in which case the completely fastened strap member will appear as indicated by the lower fastening strap member 44a in FIG. 1.

The ankle brace 10 is easily applied or fitted about the lower extremity with the ankle in the neutral position by slightly flexing the sidewall portions 16, 16a of stirrup member 14 and their corresponding airbag 20, 20a outwardly with respect to each other (about axes 32, 34) and placing the lower extremity between the sidewall portions and airbags until the heel of the foot comes to rest on the two bottommost, inwardly bent portions of airbags 20, 20a and the upwardly facing surface of base portion 18. The two sidewall portions 16, 16a are then flexed inwardly toward each other until they and the corresponding upper portions of airbags 20, 20a are brought into engagement with the medial and lateral portions of the lower extremity above the ankle. The brace may then be adjusted slightly making sure that the foot is seated comfortably within the lower portions of sidewall portions 16, 16a, and that both the medial and lateral malleolus are comfortably received within their corresponding recesses 24, 24a. Such comfort will immediately be apparent because when properly fitted there will be a clearance space or void between each malleolus and the inner wall surface of each corresponding recess in sidewall portions 16, 16a and thus, the wearer will not feel any contact pressure on either malleolus.

Once the ankle brace has been comfortably fitted, the two strap members 44, 44a may then be circumferentially wrapped about the exterior of the two sidewall portions and the lower leg and fastened in place with sufficient circumferential tension being applied to each strap member merely to cause the two upper portions of sidewall portions 16, 16a and their corresponding airbags 20, 20a to snuggly engage the lower leg.

Each airbag 20, 20a may then be inflated as by inserting a short length of tubing through self-sealing valves 40, 40a and blowing with mouth pressure. As indicated in FIG. 2, internal pressurization of each airbag will cause the inwardly facing wall portions of the airbags to radially expand toward each other until they come into engagement with the confronting irregular contours of the lower extremity, thus producing a constant pressure supporting air cushion between the irregular contours of the lower extremity and the inner surfaces 22, 22a common to the sidewall portions 16, 16a of stirrup member 14. It has been found that an internal pressure in the range of about 15 mm Hg. to about 25 mm Hg. which may easily be achieved by one or two breaths by mouth entubated through the airbag valve produces an air cushion which affords quite firm support of the lateral and medial portions of the lower extremity sufficient to limit or stabilize the ankle against inversion or eversion movements, yet which is not great enough to have any deleterious effect upon blood circulation. Surprisingly, moreover, such inflation of the air bags 20, 20a does not limit planto flexion and dorsiflexion movements of the ankle.

After inflation of each airbag 20, 20a the inflation tube is withdrawn from each valve 40, 40a thus automatically sealing the airbags and maintaining their internal pressure as described in my copending application, Ser. No. 842,961. The foot may then be dressed with a normal shoe as diagramatically indicated in FIG. 1 and a program of normal walking or running movements gradually commenced as permitted. Advantageously, the ankle brace may periodically be removed to permit whirlpool treatments, bathing, or rest and simply reapplied in the manner described above when walking or running is to resume. It will be appreciated that owing to inflation of the flexible airbags 20, 20a the flexibility of the opposed sidewall portions toward and away from each other, and the use of the circumferentially tensioned straps 44, 44a the ankle brace is automatically self-adjusting and will comfortably fit the lower extremity even as edema subsides. While an accumulation of perspiration between the confronting inner surface of each airbag and the skin surface of the lower extremity may be experienced, this may quite easily be controlled by periodic removal of the ankle brace followed by a bathing treatment or in any case, by the wearing of a conventional stocking fabricated of moisture absorbent material.

In accordance with another feature of the invention it has been discovered that dorsiflexion of the ankle while wearing the ankle brace of the present invention causes a momentary increase of the internal pressure of each airbag to as high as 40–60 mm Hg. Thus, upon normal walking or running movement, for example, there wil be manifested a cyclic pressure impulse against the lateral and medial portions of the lower extremity. Whereas, it is known that a steady-state pressure greater than about 50 mm Hg may deleteriously effect blood circulation, it is believed that a cyclic momentary increase of pressure above this level such as the periodic impulses achieved with the ankle brace of the present invention are actually beneficial in that the resulting "pumping effect" actually promotes rather than hinders blood circulation.

In an example of the preferred embodiment of the present invention ankle brace 10 is dimensioned as follows:

stirrup member height: 11.25 inches
sidewall portion width (top): 3.5 inches
sidewall portion width (bottom): 1.0 inch
base portion width: 2.0 inches
base portion length: 2.37 inches
airbag height including tucked-in portion: 12 inches
airbag width (top): 4.0 inches
airbag width (bottom): 2.5 inches
fastener strap circumference: 13.25 inches
fastener strap width: 2.0 inches The provision of the ankle brace of the present invention facilitates management of lower leg injuries in a gradual or progressive manner. Thus, in the case of fractures (e.g., tibial, fibular, malleolar) or severe sprains (e.g., collateral ligament tears), the lower extremity may first be immobilized completely by use of a long cast, followed gradually by weight bearing exercises while maintaining substantial immobilization of the lower leg (e.g., via use of a walking cast). The ankle brace of the present invention may then be used with a conventional shoe to gradually facilitate normal walking or running movements, that is substantially normal planto flexion and dorsiflexion movements, while maintaining the ankle stable against inversion or eversion. By progressively disimmobilizing the lower extremity in this regard, it is believed that management of such injuries will lead to more rapid recovery and functionality. With less severe injuries, the first and/or second stages may be omitted entirely, and the ankle brace of the present invention used exclusively (or following an initial period of management in a walking cast) to gradually promote normal planto flexion and dorsiflexion movements while maintaining the ankle stable against inversion or eversion.

Although, as mentioned above in connection with the illustrated embodiment of FIGS. 1–3, the smoothly radiused sections 28, 30 permit slight flexure of each sidewall portion 16, 16a relative to base portion 18 within the plane of view of FIG. 1, such flexure is in fact limited, and may result in fracture of the necked-down sections joining either sidewall portion to the base portion when the ankle brace is worn during vigorous exercises such as running, for example. In order to impart increased flexibility between each sidewall portion and the base portion within the plane of view of FIG. 1, i.e., about an axis perpendicular to axes 32, 34 and normal to the plane of the paper of FIG. 1, so as to avoid such fractures, it is within the contemplation of the present invention to form separate sidewall portions and base portion and to replace each necked-down section defining the flexural axes 32, 34 with a corresponding hinge in the form of a short web or length of flexible, high-tensile strength material, as for example, a strap member of woven nylon or polyester material. The hinges will provide the necessary degrees of flexibility required between the sidewall portions and the base member without sacrificing any of the functional capabilities of the one-piece stirrup member of FIGS. 1–3. In this connection, any suitable method may be employed to attach the sidewall portions to the base portion via the flexible hinges as by the use of rivets, or by use of a suitable adhesive.

Obviously, many additional modifications and alterations of the present invention will occur to those with ordinary skill. Accordingly, the present invention should be limited only by the spirit and scope of the appended claims.

I claim:

1. Orthopedic apparatus for use in connection with the lower extremity and for immobilizing the ankle against inversion or eversion while permitting planto flexion and dorsiflexion thereof comprising: a base portion and a pair of spacedapart sidewall portions attached to opposed side regions of said base portion and extending upwardly therefrom to form a generally U-shaped stirrup member adapted to be fitted about the lower extremity with the heel of the lower extremity resting on the base portion and the upstanding sidewall portions confronting corresponding opposed side portions of the lower extremity, each of said sidewall portions extending longitudinally above the ankle of the lower extremity and having a predetermined lateral extent such that the corresponding opposed longitudinally extending side edges of said sidewall portions are spaced far enough apart from each other to define a pair of openings disposed opposite the front and back portions of the lower extremity respectively when said stirrup member is fitted about the lower extremity as aforesaid, each of said sidewall portions being attached to its corresponding base portion side region by means of a flexural hinge so as to facilitate flexure of each sidewall portion toward and away from each other and toward and away from corresponding confronting side portions of the lower extremity, and a pair of flexible support members, each one of said flexible support members being substantially coextensively disposed in a juxtaposed manner with respect to the inwardly facing surface of a corresponding one of said sidewall portions so as to engage a corresponding confronting portion of the side of said lower extremity when said sidewall portions are flexed toward each other, at least one of said flexible support members comprising an inflatable bladder, and fastening means for maintaining said sidewall portions and said support members in engagement with corresponding confronting side portions of the lower extremity when said stirrup member is fitted about said lower extremity as aforesaid.

2. The apparatus of claim 1 in which said stirrup member comprises a unitary preformed member.

3. The apparatus of claim 2 in which said stirrup member is fabricated from a substantially flat sheet of thermoplastic material and said sidewall portions are bent upwardly with respect to said base portion under heat and pressure to define a pair of flexural axes lying substantially within the plane of said base portion at the bottom of each sidewall portion respectively.

4. The apparatus of claim 1 in which said sidewall portions each have a recess for receiving a corresponding malleolus on said lower extremity.

5. The apparatus of claim 1 wherein voids respectively exist between at least the lower portions of said sidewall portions and the confronting corresponding opposed side portions of the lower extremity in the region of the ankle when said stirrup member is fitted about said lower extremity as aforesaid, and said at least one inflatable bladder is adapted to be inflated to a predetermined pressure to form a pressurized cushion filling its corresponding void.

6. The apparatus of claim 5 wherein said predetermined pressure is within the range of about 15 mm Hg. to about 25 mm Hg.

7. The apparatus of claim 1 in which the flexural hinge comprises a web of flexible material.

8. The apparatus of claim 7 in which the sidewall portions are of thermoplastic material and the web is a strap of woven material attached between the base portion and each sidewall portion.

* * * * *